United States Patent [19]

Koulbanis et al.

[11] 4,010,254

[45] Mar. 1, 1977

[54] GELS BASED ON VINYL ETHER-MALEIC ANHYDRIDE COPOLYMER NEUTRALIZED BY A BASIC AMINO ACID

[75] Inventors: Constantin Koulbanis; Arlette Zabotto, both of Paris; Jean-Claude Contamin, Chilly Mazarin, all of France

[73] Assignee: Societe Anonyme dite: L'Oreal, Paris, France

[22] Filed: July 7, 1975

[21] Appl. No.: 593,243

[30] Foreign Application Priority Data

July 8, 1974 Luxembourg .......................... 70487

[52] U.S. Cl. ................................. 424/78; 252/316; 424/170; 424/364; 424/365
[51] Int. Cl.$^2$ ........................................ A61K 7/48
[58] Field of Search .............. 424/78, 365; 252/316

[56] References Cited

UNITED STATES PATENTS

| | | | |
|---|---|---|---|
| 3,499,876 | 3/1970 | Field et al. | 424/78 X |
| 3,523,998 | 8/1970 | Feinstone et al. | 424/78 |
| 3,684,776 | 8/1972 | Field et al. | 424/78 X |
| 3,823,232 | 7/1974 | Galerne | 424/72 |
| 3,836,637 | 9/1974 | Schmolka | 424/78 X |
| 3,922,341 | 11/1975 | Abegg et al. | 424/78 X |

*Primary Examiner*—Albert T. Meyers
*Assistant Examiner*—Vera C. Clarke
*Attorney, Agent, or Firm*—Cushman, Darby & Cushman

[57] ABSTRACT

A gel comprises an aqueous solution of a vinyl ether-maleic anhydride copolymer and at least one amino acid having a basic character present in an amount effective to impart to said solution a pH ranging between 3 and 9. The gel is employed as a carrier in cosmetic compositions.

10 Claims, No Drawings

GELS BASED ON VINYL ETHER-MALEIC ANHYDRIDE COPOLYMER NEUTRALIZED BY A BASIC AMINO ACID

The present invention relates to gels based on copolymers and amino acids, to their preparation and their use and principally to the preparation of cosmetic gels.

It is known that aqueous solutions of vinyl ether-maleic anhydride copolymers have the property of forming gels. These aqueous solutions have a pH which is clearly acidic and which is in the neighborhood of 2. To use gels formed by these solutions in cosmetic preparations, it is necessary to neutralize the acid groups of the polymer in solution in a manner so as to adjust the pH thereof near to neutral.

Generally, aqueous solutions of these polymers are neutralized using either mineral bases or aliphatic amines or amino alcohols, such as triethanolamine.

However, such gels, prepared in a conventional manner, have an irritant effect when they are used as carriers in compositions for application to the skin.

It has now been discovered that the irritant effect can be suppressed or greatly reduced if the acid groups of the aqueous solution of the vinyl ether-maleic anhydride copolymer are neutralized using an amino acid having basic characteristics.

Representative amino acids which can be employed include, principally, lysine, arginine, histidine and ornithine.

The present invention also relates to a gel comprising an aqueous solution of a vinyl ether-maleic anhydride copolymer and at least one amino acid having a basic character which is present in an amount effective to impart to the said solution a pH between 3 and 9, and preferably between 5 and 7.

The vinyl ether-maleic anhydride copolymers useful in the preparation of gels of the present invention are principally copolymers having a repeating unit of the formula

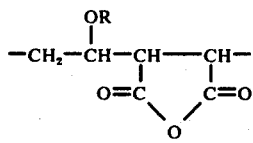

wherein R represents alkyl having 1–4 carbon atoms, and principally methyl or ethyl.

The vinyl ether-maleic anhydride copolymers employed in the preparation of the gels of the present invention can have a wide range of molecular weights. It is known, however, that the viscosity of an aqueous solution of a vinyl ether-maleic anhydride copolymer increases with the molecular weight of the copolymer. In order to avoid using an excessive quantity of copolymer, it is advantageous to select a copolymer having a molecular weight sufficiently high so as to provide a gel having a relatively high viscosity. Preferably, for the gels of the present invention, there is employed a vinyl ether-maleic anhydride copolymer which, when present in an aqueous solution at a concentration of 0.5–5 weight percent, imparts to the solution a viscosity between 1 and 1000 poises at 25° C and at a pH of 7. This viscosity measurement, which can be employed for the selection of a given vinyl ether-maleic anhydride polymer for use in accordance with the present invention, can be carried out by adjusting the pH of the aqueous solution of the copolymer to 7 by the addition thereto, for instance, of NaOH.

Further, it is known that the viscosity of vinyl ether-maleic anhydride copolymers can be increased by crosslinking these polymers with the use of a polyfunctional crosslinking agent, such as polyhydroxylated, polyaminated or polyunsaturated compounds.

However, the specific nature of the crosslinking agent is not controlling. What is important is that the degree of crosslinking be sufficiently limited so that while the crosslinking leads to a viscosity increase, it does not lead to the insolubility of the copolymer in water.

Thus, when it is desired to utilize in the present invention a crosslinked vinyl ether-maleic anhydride polymer, it is advantageous then to employ a crosslinked copolymer wherein the degree of crosslinking is sufficiently limited so that the specific viscosity falls within the aforementioned limits.

The amino acids usefully employed in the preparation of the gels of the present invention include those having the formula

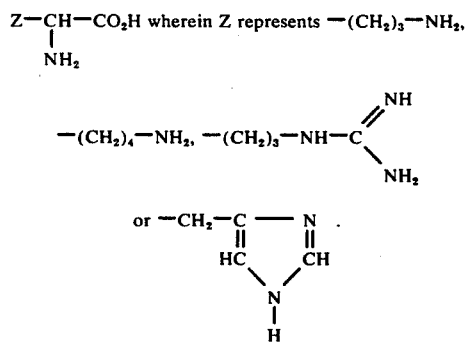

In the gels of the present invention, the vinyl ether-maleic anhydride copolymer is generally present in an amount effective to impart to the gel a viscosity ranging between 10 and 100 poises, and preferably between 20 and 60 poises.

Representative specific copolymers employed in the preparation of the gels of the present invention include those sold under the tradenames Viscofas X 100,000, Viscofas L 100 as well as Gantrex AN 149 and 169.

The present invention also relates to a process for preparing the above-defined gels. This process comprises, generally, dissolving the vinyl ether-maleic anhydride copolymer in water and adding the selected amino acid in an amount effective to impart to the resulting gel a pH between 3 and 9 and preferably between 5 and 7.

This process can be effected in accordance with one of the two embodiments described below.

According to a first embodiment, the copolymer is initially dissolved in water and then the amino acid is added thereto in an amount effective to adjust the pH thereof to the desired value.

The dissolution of the copolymer can be effected at a temperature greater or equal to about 20° C and lower than 100° C. The speed or rate of dissolution of the copolymer is increased when using warm water. Preferably the temperature of the water employed is between about 90° and 99° C. During the dissolution of the copolymer, it is advantageous to vigorously agitate the water so as to avoid the formation of agglomerates. The time required for the dissolution of the copolymer generally ranges between about 25 and 40 minutes, depending of course on such factors as the degree of polymerization of the copolymer used when operating at 95° C.

Preferably the resulting solution of the copolymer is cooled near 20° C before adding the amino acid thereto.

The addition of the amino acid is carried out by progressively introducing an aqueous solution of the amino acid into the aqueous solution of the copolymer.

The quantity of copolymer used depends principally on the desired ultimate viscosity of the resulting product. This quantity can be determined in a very simple manner as a function of the volume of water employed, taking into account the fact that the volume of water present in the final gel is the sum of the volume of water used to dissolve the copolymer and the volume of water used to dissolve the basic amino acid employed for neutralization.

According to the second embodiment, the basic amino acid is dissolved in the totality of the water to be employed. Then the vinyl ether-maleic anhydride copolymer is progressively added thereto with agitation until a gel having the desired viscosity is attained.

To effect this second embodiment, the basic amino acid can be dissolved in the totality of the water to be used at ambient temperature, and the resulting solution is then heated to a temperature between about 90° and 99° C. Thereafter, the copolymer is progressively added to the heated solution with sufficient agitation so as to avoid the formation of agglomerates.

Of course, the quantity of amino acid added is predetermined so as to impart to the resulting gel the desired pH.

The present invention also relates to a cosmetic composition comprising as the carrier or excipient therefor the gel as defined above.

These cosmetic compositions are principally those employed for application to the skin and are provided in the form of a gel, fluid jellified lotion or an emulsion, characterized by the fact that they include, as the excipient or carrier, a gel such as defined above.

The compositions of the present invention are principally gels such as makeup remover gels for the face or eyes, slenderizing gels, refreshing gels, gels for the treatment of ecchymosis, etc; and fluid jellified lotions such as skin refreshing lotions, makeup remover lotions, tonic lotions or resting lotions for the eyes or skin.

It is possible to prepare directly a composition such as defined above, notably a cosmetic composition by utilizing either one of the two process embodiments defined above.

To prepare directly a composition in accordance with the first process embodiment, the copolymer is added to a portion of the water required in the preparation of the composition; then the resulting solution is neutralized with the amino acid; finally the active ingredients or various desired additives are added thereto, directly, or in the form of an aqueous solution thereof.

When the composition contains a preservative agent, it is generally dissolved in the water before the addition of the copolymer.

To prepare directly a composition in accordance with the second process embodiment, the amino acid is dissolved in a major portion of the water to be used in formulating the composition; then the copolymer is added thereto; and finally the active ingredients and/or various desired additives are added either directly or in the form of an aqueous solution.

The expression "the major portion of the water" means the totality of the water contained in the composition minus the quantity of water employed to solubilize the active components and/or desired additives so as to provide a preliminary solution thereof.

When the composition contains a preservative agent, it is dissolved in the water before the addition of the amino acid.

Advantageously when a composition having a high viscosity such as a gel is desired, preferably the first process embodiment is employed.

The compositions of the present invention can also be provided in the form of an emulsion having an oily phase which is added to the previously described gel. It has been observed that the gels of the present invention confer a good stability characteristic to emulsions such as, principally, those of the oil-in-water type. These emulsions can comprise such cosmetic compositions as, for instance, skin creams, makeup remover milks, body milks and the like.

To prepare these compositions in the form of emulsions, the copolymer is dissolved in a portion of the water which is preferably heated to between about 90° and 99° C. The resulting solution is then cooled, if desired, to ambient temperature and subsequently neutralized by the addition of the amino acid thereto. The oily phase is then added thereto with vigorous agitation thereby producing the said emulsion. It is sometimes preferable, notably for the preparation of thick creams, to add the amino acid only after making the emulsion by the addition of the oily phase.

The compositions of the present invention can contain one or more active components, the nature of which depends obviously on the ultimate use of the cosmetic composition. Further these compositions can contain various components, such as surface active agents, perfumes, dyes, preservatives and the like.

The following non-limiting examples are given to illustrate the present invention. In these examples, the preservative agent employed is methyl para hydroxy benzoate or propyl para hydroxy benzoate, or a 50:50 mixture thereof. Unless otherwise indicated, all parts and percentages are by weight.

The polymers used in these examples exhibit the following characteristics:

Viscofas X 100,000 is a crosslinked methyl vinyl ether-maleic anhydride copolymer, a 5% aqueous solution of which has a viscosity of 100,000 cp at 25° C at a pH of 7.

Viscofas L 100 is a linear copolymer of methyl vinyl ether and maleic anhydride, a 5% aqueous solution of which has a viscosity of 4000 ± 1000 cp (25° C; pH 7).

EXAMPLE 1

88.6 g of sterile demineralized water are heated on a water bath. When the water reaches a temperature of 95° C it is agitated using a helical type agitator so as to produce therein a vortex. There is then added, progressively, by sprinkling, 0.7 g. of Viscofas X 100,000 thereby avoiding the formation of agglomerates.

After 30 minutes at 95° C, the hydrolysis of the copolymer is complete and the resulting solution which is glossy and viscous is cooled and left to stand. Thereafter there is slowly added a solution of 0.7 g of L-arginine in 10 g of water accompanied by moderate agitation until a thick gel, transparent and glossy, is produced.

EXAMPLE 2

1.2 g of L-lysine are dissolved in 97.8 g of sterile demineralized water. This solution which is heated to 95° C is then agitated so as to produce a vortex and there is then added progressively, by sprinkling, into the vortex formed, 1 g of Gantrez AN 169. After about 40 minutes, the resulting solution which is homogeneous, transparent and slightly viscous, is cooled.

EXAMPLE 3

A solution of 0.3 g of a preservative agent in 77.5 g of water is heated on a water bath. When the temperature of the solution reaches 95° C, the solution is agitated in a manner to produce a vortex. There is then slowly added thereto, by sprinkling so as to obtain a good dispersion, 0.60 g of Viscofas X 100,000. The resulting mixture is agitated for 30 minutes while maintaining the temperature at 95° C.

The resulting solution is then cooled and left to stand so as to eliminate air bubbles therefrom.

There is then progressively added to the solution with moderate agitation, a solution of 0.50 g of L-arginine in 5 g of sterile demineralized water. The solution of the copolymer thickens and becomes transparent. A solution of 0.01 g of ethylene diamine tetra acetic acid in 5 g of sterile demineralized water and a solution of 1 g of non-ionic surface active agent in 10 g of sterile demineralized water are added thereto while maintaining moderate agitation until a glossy and homogeneous product is produced.

The non-ionic surface active agent can be cetyl alcohol polyoxyethylenated with 20 moles of ethylene oxide, or stearyl alcohol polyoxyethylenated with 20 moles of ethylene oxide, or a mixture of these two compounds.

There is thus obtained a makeup remover gel for the face having the following composition:

| | |
|---|---|
| Viscofas X 1000,000 | 0.60 g |
| Ethylene diamine tetra acetic acid | 0.01 g |
| L-arginine | 0.50 g |
| Non-ionic surface active agent | 1.00 g |
| Preservative | 0.30 g |
| Sterile demineralized water | 97.59 g |
| | 100.00 g |

EXAMPLE 4

In the same manner as described in Example 3, there are prepared, in accordance with the first process embodiment of the invention, cosmetic compositions in the form of a gel, of the following formulations:

| | | |
|---|---|---|
| (a) | Eye makeup remover gel: | |
| | Viscofas X 100,000 | 0.40 % |
| | Ethylene diamine tetra acetic acid | 0.01 % |
| | Arginine | 0.40 % |
| | Polyethylene glycol | 12.00 % |
| | Water + preservative | 87.19 % |
| | | 100.00 % |
| (b) | Slenderizing gel: | |
| | Viscofas X 100,000 | 0.80 % |
| | Ethylene diamine tetra acetic acid | 0.01 % |
| | Histidine | 0.65 % |
| | Algae extract | 3.00 % |
| | Boleau extract | 2.00 % |
| | Water + preservative | 93.54 % |
| | | 100.00 % |
| (c) | Limb refreshing gel: | |
| | Viscofas X 100,000 | 0.70 % |
| | Ethylene diamine tetra acetic acid | 0.01 % |
| | Lysine | 0.60 % |
| | Extract of Calendula | 10.00 % |
| | Extract of horse chestnut | 2.00 % |
| | Extract of parsley | 0.10 % |
| | Water + preservative | 86.59 % |
| | | 100.00 % |
| (d) | Gel for the treatment of ecchymosis: | |
| | Viscofas X 100,000 | 0.70 % |
| | Ethylene diamine tetra acetic acid | 0.01 % |
| | Histidine | 0.60 % |
| | Aescine | 1.00 % |
| | Water + preservative | 97.69 % |
| | | 100.00 % |
| (e) | Eye resting gel: | |
| | Viscofas X 100,000 | 0.50 % |
| | Ethylene diamine tetra-acetic acid | 0.01 % |
| | Extract of camomille | 2.00 % |
| | Extract of Bleuet | 2.00 % |
| | Arginine | 0.50 % |
| | Allantoin | 0.10 % |
| | Water + preservative | 94.89 % |
| | | 100.00 % |

EXAMPLE 5

The following compositions have been prepared in accordance with the process of the present invention:

| | | |
|---|---|---|
| (a) | Body refreshing lotion: | |
| | Gantrez AN 169 | 0.40 % |
| | Ethylene diamine tetra acetic acid | 0.01 % |
| | Arginine | 0.35 % |
| | Rose water | 30.00 % |
| | Alcohol-ethyl | 5.00 % |
| | Water + preservative + dye | 64.24 % |
| (b) | Eye resting lotion: | |
| | Viscofas L 100 | 0.40 % |
| | Ethylene diamine tetra acetic acid | 0.01 % |
| | Arginine | 0.40 % |
| | Camomille water | 20.00 % |
| | Allantoin | 0.10 % |
| | Extract of horse chestnut | 1.00 % |
| | Water + preservative | 78.09 % |
| | | 100.00 % |
| (c) | Makeup remover tonic for the body: | |
| | Gantrex AN 149 | 0.50 % |
| | Ethylene diamine tetra acetic acid | 0.01 % |
| | Lysine | 0.40 % |
| | Glycerine | 2.00 % |
| | Rose water | 20.00 % |
| | Cetyl alcohol polyoxyethylnated with 20 moles of ethylene oxide | 0.50 % |
| | Water + preservative + dye | 76.59 % |

EXAMPLE 6

The following emulsion compositions in accordance with the present invention have been prepared:

| | | |
|---|---|---|
| (a) | Daily cosmetic cream for oily skin: | |
| | Brij 56 (non-ionic surface active agent sold by Atlas Powder Co.) | 2.00 % |

| | | |
|---|---|---|
| | -continued | |
| | Cetyl alcohol | 1.00 % |
| | Mineral oil | 10.00 % |
| | Viscofas × 100,000 | 0.40 % |
| | Arginine | 0.35 % |
| | Water + preservative | 86.25 % |
| | | 100.00 % |
| (b) | Makeup remover milk: | |
| | Oil of petrolatum | 10.00 % |
| | Isopropyl palmitate | 5.00 % |
| | Glycerol stearate | 2.00 % |
| | Stearic acid | 1.40 % |
| | Triethanolamine | 0.70 % |
| | Viscofas × 100,000 | 0.60 % |
| | Lysine | 0.50 % |
| | Water + preservative | 79.80 % |
| | | 100.00 % |
| (c) | Body milk: | |
| | Triethanolamine stearate | 2.00 % |
| | Mineral oil | 10.00 % |
| | Arlacel 165 (non-ionic emulsifying agent sold by Atlas Powder Co.) | 2.00 % |
| | Viscofas × 100,000 | 0.30 % |
| | Arginine | 0.25 % |
| | Water + preservative | 95.45 % |
| (d) | Soap rinsing cream: | |
| | Triethanolamine stearate | 12.00 % |
| | Mineral oil | 20.00 % |
| | Propylene glycol | 10.00 % |
| | Viscofas × 100,000 | 0.40 % |
| | Arginine | 0.35 % |
| | Water + preservative | 57.25 % |
| | | 100.00 % |

The compositions in the form of emulsions described above have been prepared in accordance with the process previously indicated. It will be noted that, in the case of creams (a and d), the basic amino acid (arginine) was added only after preparing the emulsion.

EXAMPLE 7

Irritant effect study: Index of Primary Irritation

The principle of this test consists in noting the skin reaction after a single application of the product on the shaved skin of rabbits.

The degree of erythema and the edema produced are noted and the degree of each is rated in accordance with a conventional numeric scale ranging from 0 to 4.

A product which has no primary irritating effect is given a rating of 0.

A very irritating product, producing serious erythema and significant edema, is given the maximum rating, i.e. 8.

This test is described in detail in the decree of April 5, 1971 published in the Journal Officiel de la Republique francaise of April 21, 1971.

Using this test, a vinyl ether-maleic anhydride copolymer neutralized by triethanolamine is compared to the same copolymer neutralized, however, in accordance with the present invention with arginine.

The following results were obtained:

| Copolymer | Neutralized by: | I.I.P. |
|---|---|---|
| Viscofas × 100,000 | Triethanolamine | 2.10/8 |
| Viscofas × 100,000 | Arginine | 1.53/8 (−30%) |

What is claimed is:

1. A gel comprising an aqueous solution of a vinyl ether-maleic anhydride copolymer, a 0.5–5 weight percent aqueous solution of said copolymer having a viscosity ranging between 1 and 1000 poises measured at 25° C and at a pH of 7, said copolymer having a repeating unit of the formula

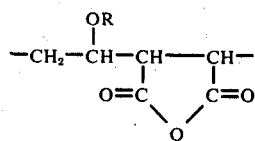

wherein R is alkyl having from 1–4 carbon atoms, and at least one amino acid having a basic character, said copolymer being present in an amount such that the viscosity of said gel is between 10 and 100 poises and said amino acid being present in an amount effective to impart to said solution a pH ranging between 3 and 9.

2. The gel of claim 1 wherein said amino acid is present in an amount effective to impart to said solution a pH ranging between 5 and 7.

3. The gel of claim 1 wherein said amino acid has the formula

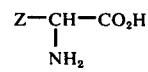

wherein Z represents a member selected from the group consisting of

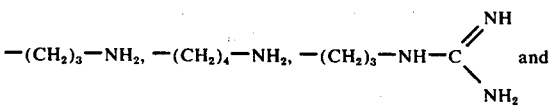

and

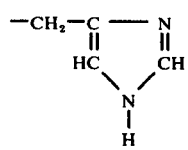

4. A process for preparing the gel of claim 1 comprising heating water to a temperature between about 90° and 99° C; adding said copolymer to the resulting heated water with agitation until said copolymer has dissolved; cooling the resulting solution to a temperature near 20° C; progressively adding to the resulting cooled solution the said amino acid in the form of an aqueous solution to adjust the pH thereof to the desired value.

5. A process for preparing the gel of claim 1 comprising initially dissolving said amino acid in the totality of the water being employed at ambient temperature, said amino acid being added in an amount effective to impart to the finally resulting gel the desired pH; heating the resulting solution to a temperature between about 90° and 99° C; progressively adding with agitation to the resulting heated solution the said copolymer in an amount sufficient to impart the desired viscosity to the resulting gel.

6. A cosmetic composition for application to the skin comprising at least one cosmetic component to be applied to the skin and as an excipient therefor, the gel of claim 1.

7. A process for producing the cosmetic composition of claim 6 comprising heating to a temperature between about 90° and 99° C a portion of the water necessary for the preparation of said composition; adding said copolymer to the resulting heated water with agitation until said copolymer is dissolved therein; cooling the resulting solution to a temperature near 20° C; progessively adding to the resulting cooled solution the said amino acid in the form of an aqueous solution; and thereafter adding the said cosmetic component thereto.

8. A process for producing the cosmetic composition of claim 6 comprising dissolving the said amino acid in a major portion of the water employed to produce said composition at ambient temperature; heating the resulting solution to a temperature between about 90° and 99° C; adding said copolymer with agitation to the resulting heated solution; and thereafter adding the said cosmetic component thereto.

9. A process for producing the cosmetic composition of claim 6 in emulsion form comprising heating a portion of the water employed to produce said composition to a temperature between about 90 and 99° C; progessively adding the said copolymer to the resulting heated water with agitation until said copolymer is dissolved therein; cooling the resulting solution to a temperature near 20° C; adding to the resulting cooled solution the said amino acid to adjust the pH thereof to the desired value; and then adding thereto said cosmetic component which is an oily phase with vigorous agitation so as to produce said composition in emulsion form.

10. A process for producing the cosmetic composition of claim 6 in the form of a thick cream comprising heating a portion of the water employed to produce said composition to a temperature between about 90° and 99° C; progressively adding the said copolymer to the resulting heated water with agitation until said copolymer is dissolved therein; cooling the resulting solution to a temperature near 20° C; adding thereto said cosmetic component which is an oily phase with vigorous agitation so as to produce an emulsion and then adding said amino acid to said emulsion to neutralize the same, thereby producing said composition in the form of a thick cream.

* * * * *